(12) United States Patent
Takahashi

(10) Patent No.: US 10,389,918 B2
(45) Date of Patent: Aug. 20, 2019

(54) DOCUMENT READING UNIT THAT ENSURES DISTINGUISHING AND READING FLUORESCENT COLOR

(71) Applicant: Kyocera Document Solutions Inc., Osaka (JP)

(72) Inventor: Masayoshi Takahashi, Osaka (JP)

(73) Assignee: Kyocera Document Solutions Inc., Osaka (JP)

( * ) Notice: Subject to any disclaimer, the term of this patent is extended or adjusted under 35 U.S.C. 154(b) by 0 days.

(21) Appl. No.: 15/887,992

(22) Filed: Feb. 3, 2018

(65) Prior Publication Data

US 2018/0227462 A1   Aug. 9, 2018

(30) Foreign Application Priority Data

Feb. 3, 2017   (JP) ................. 2017-018368

(51) Int. Cl.
*H04N 1/60* (2006.01)
*H04N 1/48* (2006.01)
(Continued)

(52) U.S. Cl.
CPC .......... *H04N 1/6027* (2013.01); *G01N 21/64* (2013.01); *H04N 1/00803* (2013.01); *H04N 1/0281* (2013.01); *H04N 1/02895* (2013.01); *H04N 1/04* (2013.01); *H04N 1/0423* (2013.01); *H04N 1/4072* (2013.01); *H04N 1/484* (2013.01); *H04N 1/486* (2013.01); *H04N 2201/0094* (2013.01);
(Continued)

(58) Field of Classification Search
CPC .. G01N 21/64; H04N 1/00803; H04N 1/0281; H04N 1/02895; H04N 1/04; H04N 1/0423; H04N 1/4072; H04N 1/484; H04N 1/486; H04N 1/6027; H04N 2201/0094; H04N 2201/02493; H04N 2201/0458
USPC .......................... 358/505, 513–515, 475, 50
See application file for complete search history.

(56) References Cited

U.S. PATENT DOCUMENTS 5,250,980 A * 10/1993 Yakubo ............... G03B 27/526
                                                                 355/32
5,768,023 A *  6/1998 Sawaki .................... B41J 2/465
                                                                 359/622
(Continued)

FOREIGN PATENT DOCUMENTS

JP          H09-98302 A      4/1997

*Primary Examiner* — Negussie Worku
(74) *Attorney, Agent, or Firm* — HEA Law PLLC

(57) ABSTRACT

A document reading unit includes an R light source, a G light source, a B light source, a UV light source, a lighting control unit, a first photoelectric conversion element, a second photoelectric conversion element, a lens, and an output unit. The first photoelectric conversion element includes an M filter. The second photoelectric conversion element includes a G filter. The output unit outputs outputs of the first photoelectric conversion element and the second photoelectric conversion element at the time of simultaneous lighting of the R and G light sources and an output of the first photoelectric conversion element at the time of simultaneous lighting of the B and UV light sources as the image data, and outputs an output of the second photoelectric conversion element at the time of simultaneous lighting of the B and UV light source as fluorescent color data indicating a fluorescent color region.

3 Claims, 5 Drawing Sheets

(51) Int. Cl.
*H04N 1/00* (2006.01)
*H04N 1/407* (2006.01)
*H04N 1/04* (2006.01)
*G01N 21/64* (2006.01)
*H04N 1/028* (2006.01)

(52) U.S. Cl.
CPC .............. *H04N 2201/02493* (2013.01); *H04N 2201/0458* (2013.01)

(56) References Cited

U.S. PATENT DOCUMENTS

| | | | |
|---|---|---|---|
| 6,232,997 B1* | 5/2001 | Nakamura | B41J 2/4476 347/120 |
| 6,371,908 B1* | 4/2002 | Furusawa | H04N 9/045 348/E9.01 |
| 10,274,369 B2* | 4/2019 | Brunson | G01J 3/42 |
| 2003/0072040 A1* | 4/2003 | Okamura | H04N 1/401 358/474 |
| 2006/0132777 A1* | 6/2006 | Hubble, III | G01J 3/10 356/402 |
| 2009/0051944 A1* | 2/2009 | Bracke | B41J 2/04506 358/1.9 |
| 2009/0116080 A1* | 5/2009 | Maruyama | H04N 1/02835 358/475 |
| 2009/0200477 A1* | 8/2009 | Takabatake | H04N 1/0286 250/370.08 |
| 2010/0114264 A1* | 5/2010 | Lechthaler | A61N 5/0616 607/88 |
| 2010/0114266 A1* | 5/2010 | Lechthaler | A61N 5/0616 607/94 |
| 2011/0096370 A1* | 4/2011 | Okamoto | H04N 1/00795 358/444 |
| 2013/0328946 A1* | 12/2013 | Zenker | G09F 9/35 345/690 |
| 2017/0202445 A1* | 7/2017 | Sakai | A61B 1/06 |

* cited by examiner

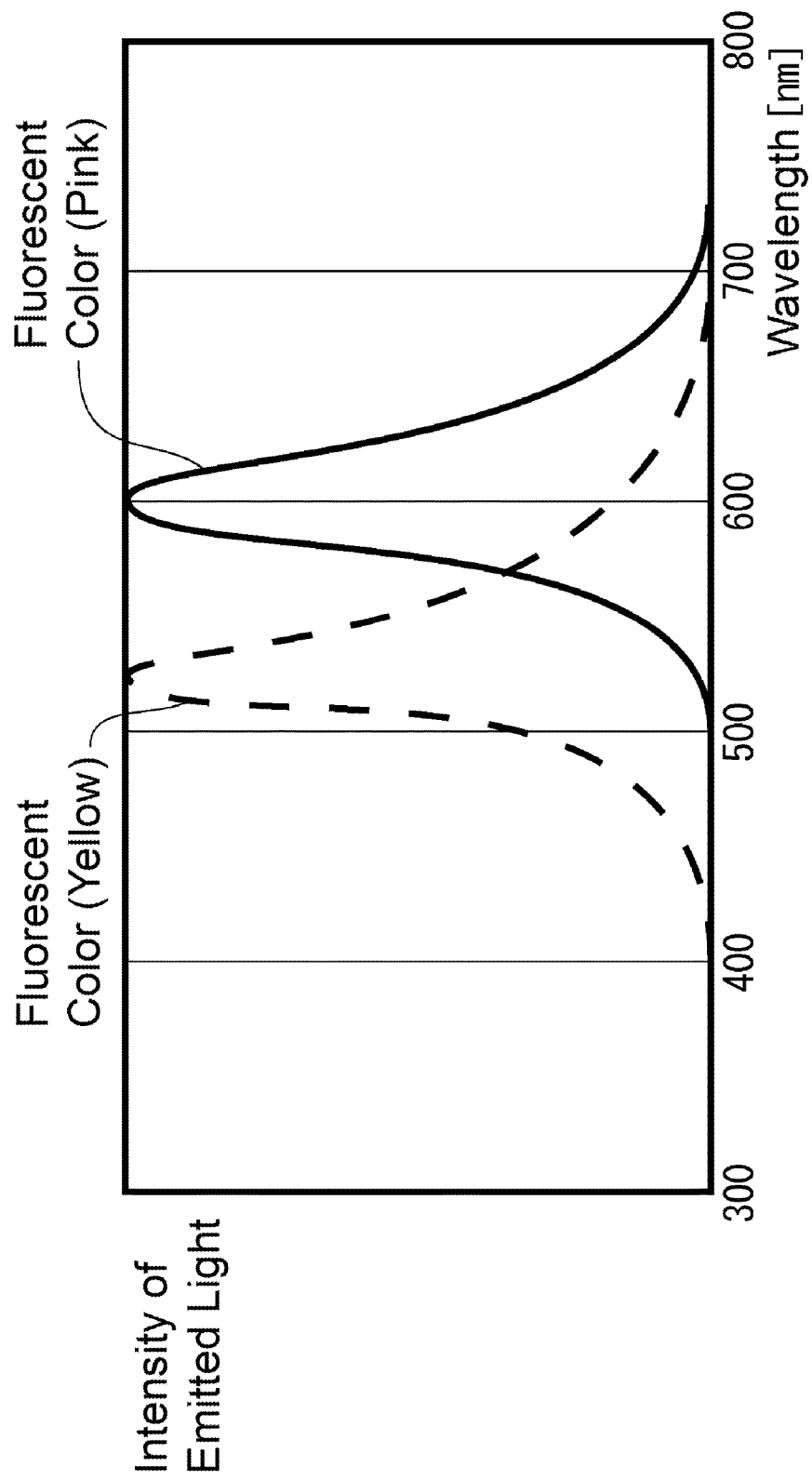

DOCUMENT READING UNIT THAT ENSURES DISTINGUISHING AND READING FLUORESCENT COLOR

INCORPORATION BY REFERENCE

This application is based upon, and claims the benefit of priority from, corresponding Japanese Patent Application No. 2017-018368, filed in the Japanese Patent Office on Feb. 3, 2017, and the entire contents of which are incorporated herein by reference.

BACKGROUND

Unless otherwise indicated herein, the description in this section is not prior art to the claims in this application and is not admitted to be prior art by inclusion in this section.

While a full-color document is read as image data where red (R), green (G), and blue (B) are expressed by luminance levels, its color cannot be determined whether it is a fluorescent color or not based on the luminance level. Then, there is a proposed technique where the addition of reading with an ultraviolet light distinguishes and reads a fluorescent color to improve the reproducibility of the fluorescent color.

SUMMARY

A document reading unit according to one aspect of the disclosure reads an original document as image data expressed by luminance signals of RGB. The document reading unit includes an R light source, a G light source, a B light source, a UV light source, a lighting control unit, a first photoelectric conversion element, a second photoelectric conversion element, a lens, and an output unit. The R light source irradiates the original document with a red light. The G light source irradiates the original document with a green light. The B light source irradiates the original document with a blue light. The UV light source irradiates the original document with an ultraviolet light. The lighting control unit switches between simultaneous lighting of the R light source and the G light source and simultaneous lighting of the B light source and the UV light source when reading one line in the original document. The first photoelectric conversion element includes an M filter. The M filter transmits the red light and the blue light and cuts off the green light and the ultraviolet light. The second photoelectric conversion element includes a G filter. The G filter transmits the green light and cuts off the red light, the blue light, and the ultraviolet light. The lens guides reflected lights from the original document to the first photoelectric conversion element and the second photoelectric conversion element. The output unit outputs outputs of the first photoelectric conversion element and the second photoelectric conversion element at the time of simultaneous lighting of the R light source and the G light source and an output of the first photoelectric conversion element at the time of simultaneous lighting of the B light source and the UV light source as the image data. The output unit outputs an output of the second photoelectric conversion element at the time of simultaneous lighting of the B light source and the UV light source as fluorescent color data indicating a fluorescent color region.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

BRIEF DESCRIPTION OF THE DRAWINGS

FIG. 6 illustrates spectral spectrum examples of radiated lights radiated from a fluorescent color excited by the UV light source according to the one embodiment.

DETAILED DESCRIPTION

Figure 1:
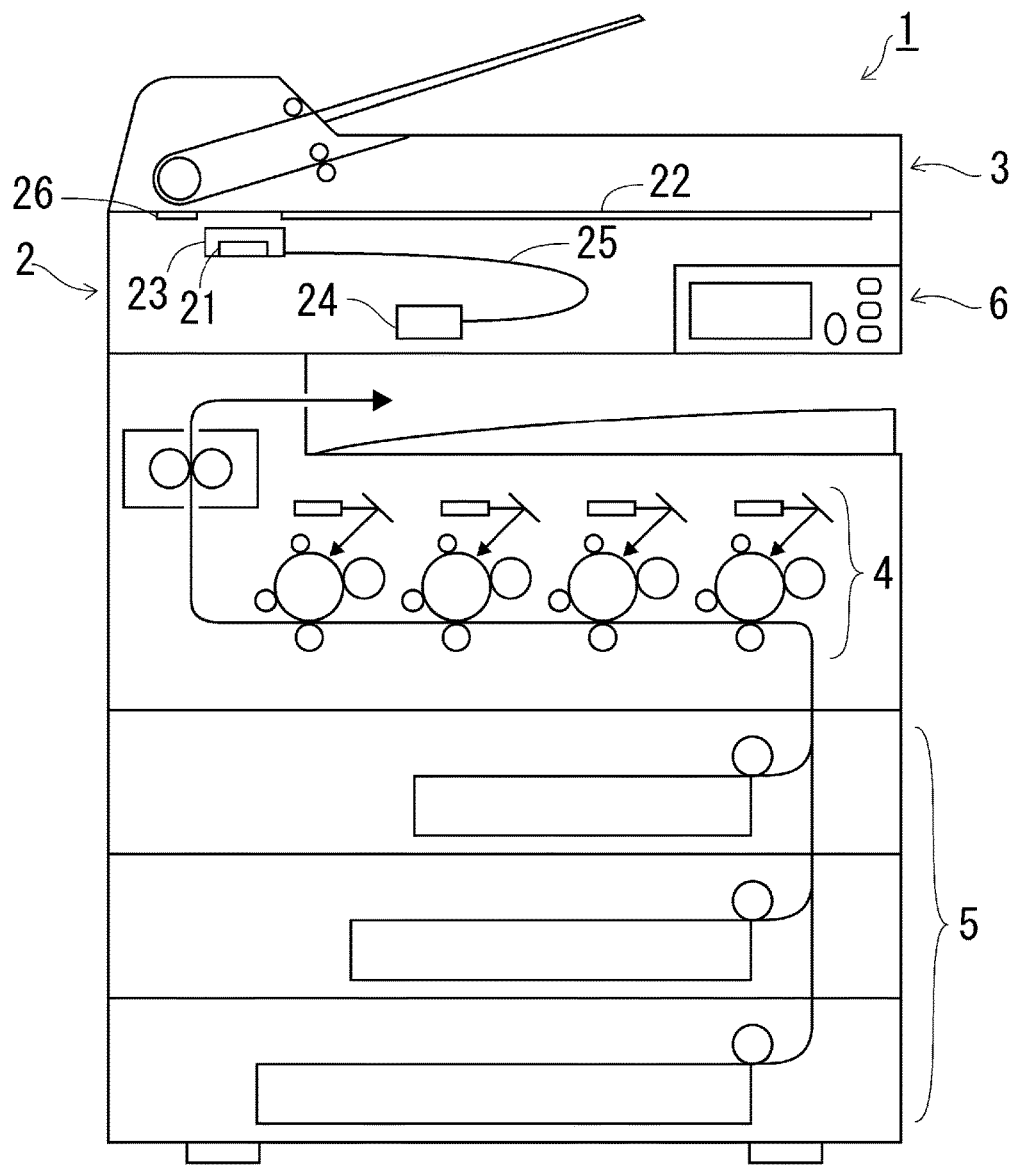
FIG. 1 schematically illustrates a cross section of an image processing apparatus including a document reading unit according to one embodiment of the disclosure.

Example apparatuses are described herein. Other example embodiments or features may further be utilized, and other changes may be made, without departing from the spirit or scope of the subject matter presented herein. In the following detailed description, reference is made to the accompanying drawings, which form a part thereof.

The example embodiments described herein are not meant to be limiting. It will be readily understood that the aspects of the present disclosure, as generally described herein, and illustrated in the drawings, can be arranged, substituted, combined, separated, and designed in a wide variety of different configurations, all of which are explicitly contemplated herein.

The following describes an embodiment of the disclosure in detail with reference to the drawings. In the following embodiment, like reference numerals are designated to configurations that indicate similar functions.

The embodiment relates to an image processing apparatus 1, such as a copier and a multifunctional peripheral (MFP). With reference to FIG. 1, the image processing apparatus 1 includes a document reading unit 2, a document feeding unit 3, an image forming unit 4, a recording sheet feeding unit 5, and an operation unit 6.

The document reading unit 2 includes a contact imaging sensor (CIS) 21, a reading unit 23, a reading control unit 24, and an FFC 25. The CIS 21 includes light sources such as LEDs, which irradiate an imaging target with lights, photoelectric conversion elements including a plurality of imaging devices arranged in a main-scanning direction, and an optical component such as a lens. The reading unit 23 includes the CIS 21 and reciprocates in a sub-scanning direction along a back surface of a contact glass 22 on which an original document is placed. The reading control unit 24 controls an image reading operation by the document reading unit 2. The FFC 25 connects the reading unit 23 to the reading control unit 24.

The document feeding unit 3 functions as a cover that opens and closes the top surface of the contact glass 22, and the document feeding unit 3 is opened upward to open the top surface of the contact glass 22, so as to be ready for placing the original document on the contact glass 22.

When reading of the original document is instructed through the operation unit 6 in a state where the original document is not placed on the document feeding unit 3 or an open state where the document feeding unit 3 is opened, the original document placed on the contact glass 22 is read. When reading the original document placed on the contact glass 22, the reading unit 23 is moved to the position opposed to the contact glass 22, and then reads the original document placed on the contact glass 22 while scanning in the sub-scanning direction orthogonal to the main-scanning direction to obtain image data, so as to output the obtained image data to the image forming unit 4.

When reading of the original document is instructed through the operation unit 6 in a state where the original document is placed on the document feeding unit 3, the original document conveyed by the document feeding unit 3 is read. When the original document conveyed by the document feeding unit 3 is read, the reading unit 23 is moved to the position opposed to a slit glass 26 located in a document conveying path, and then reads the original document via the slit glass 26 in synchronization with a document conveying operation by the document feeding unit 3 to obtain image data, so as to output the obtained image data to the image forming unit 4.

The image forming unit 4 forms a toner image based on image data and transfers the formed toner image onto the recording sheet conveyed from the recording sheet feeding unit 5. The image forming unit 4 repeatedly executes an electrostatic latent image process on respective colors of yellow, magenta, cyan, and black to form a yellow toner image, a magenta toner image, a cyan toner image, and a black toner image to superimpose these images, thus forming a color image on the recording sheet. The image forming unit 4 is not limited to an electrophotographic method, may be an inkjet recording method, and may be another recording method or printing method.

The operation unit 6 includes: a function as a display that displays, for example, a state of the image processing apparatus 1; and a function as an input unit that accepts a setting of the image processing apparatus 1 and an input of an operation instruction, and is constituted of, for example, various kinds of operation keys and a touch panel.

Figure 2:
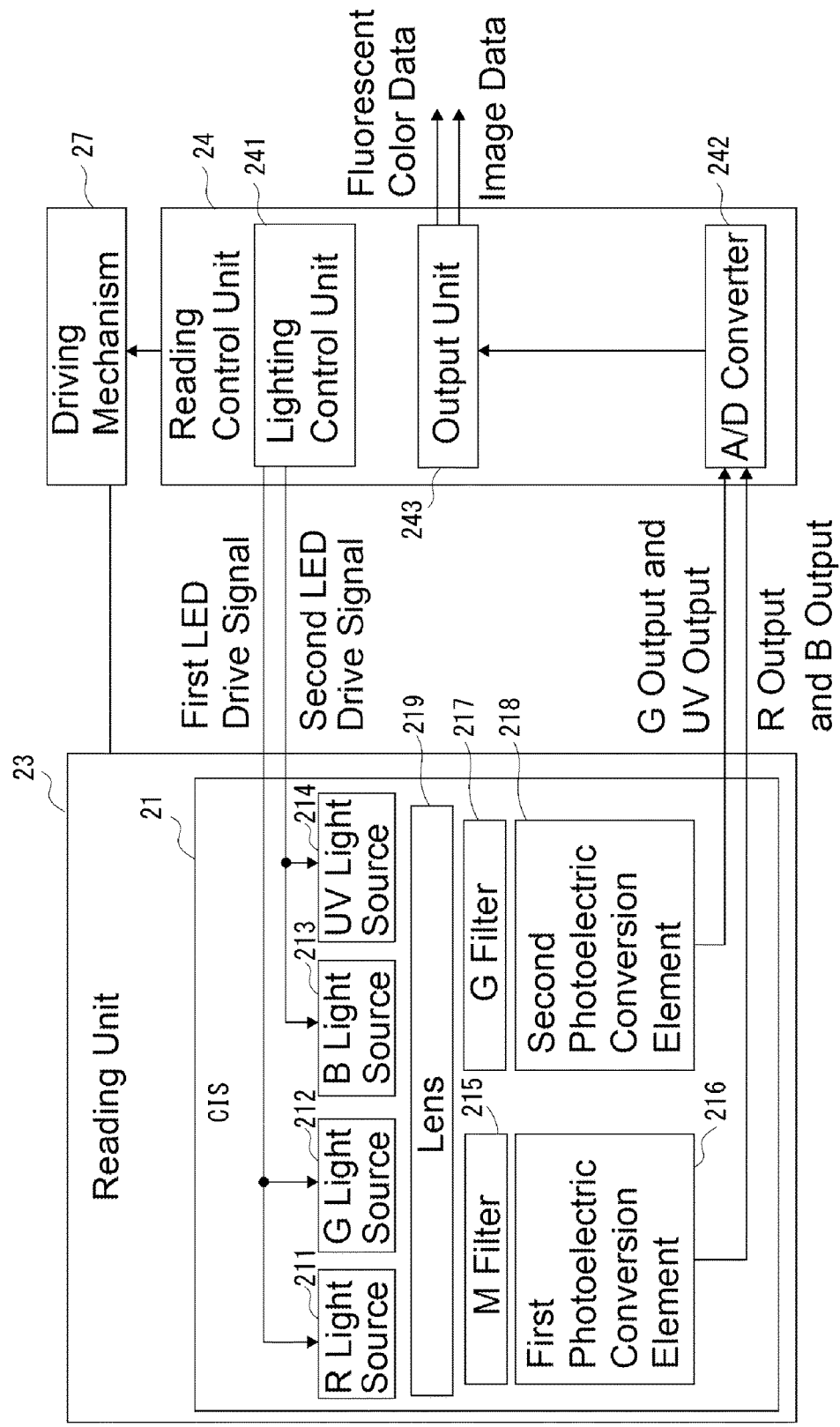
FIG. 2 illustrates a block diagram illustrating a schematic configuration of the document reading unit according to the one embodiment.

With reference to FIG. 2, the document reading unit 2 includes the reading unit 23, which includes the CIS 21, the reading control unit 24, and a driving mechanism 27, which reciprocates the reading unit 23 by the control of the reading control unit 24 in the sub-scanning direction.

With reference to FIG. 2, the CIS 21 includes an R light source 211, a G light source 212, a B light source 213, a UV light source 214, a first photoelectric conversion element 216, a second photoelectric conversion element 218, and a lens 219. The R light source 211 irradiates the original document with a red light (an R light). The G light source 212 irradiates the original document with a green light (a G light). The B light source 213 irradiates the original document with a blue light (a B light). The UV light source 214 irradiates the original document with an UV light (ultraviolet light). The first photoelectric conversion element 216 includes an M filter 215 that transmits magenta (M). The second photoelectric conversion element 218 includes a G filter 217 that transmits green (G). The lens 219 guides reflected lights from the original document to the first photoelectric conversion element 216 and the second photoelectric conversion element 218.

The reading control unit 24 is an arithmetic processing circuit such as a microcomputer that includes, for example, a central processing unit (CPU), a read-only memory (ROM), and a random-access memory (RAM). In the ROM, a control program for performing an operation control of the document reading unit 2 is stored. The reading control unit 24 reads the control program stored in the ROM to load the control program to the RAM, so as to perform the control of the document reading unit 2.

The reading control unit 24 functions as a lighting control unit 241, an A/D converter 242, and an output unit 243. The lighting control unit 241 supplies the CIS 21 with a first LED drive signal and a second LED drive signal. The first LED drive signal controls lighting of the R light source 211 and the G light source 212. The second LED drive signal controls lighting of the B light source 213 and the UV light source 214. The A/D converter 242 converts an analog image signal from the CIS 21 into digital data. The output unit 243 outputs the image signal converted into the digital data to the image forming unit 4. The reading control unit 24 may be partially or entirely configured as an individual IC (a semiconductor integrated circuit), which is designed exclusively for its execution.

Figure 3A:
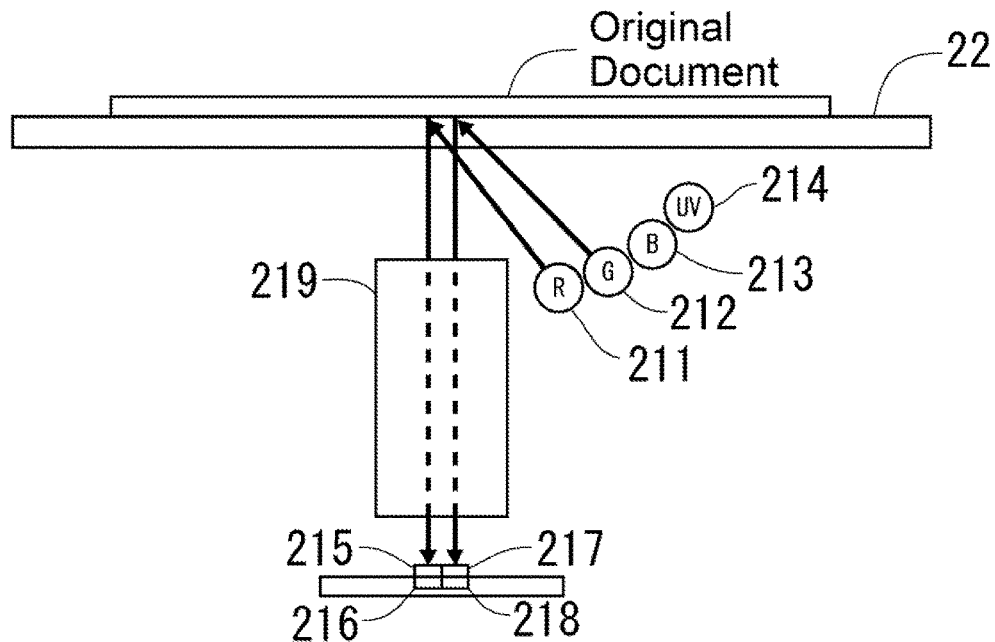
FIGS. 3A and 3B illustrate explanatory diagrams illustrating a reading operation by a contact imaging sensor (CIS) according to the one embodiment.
Figure 3B:
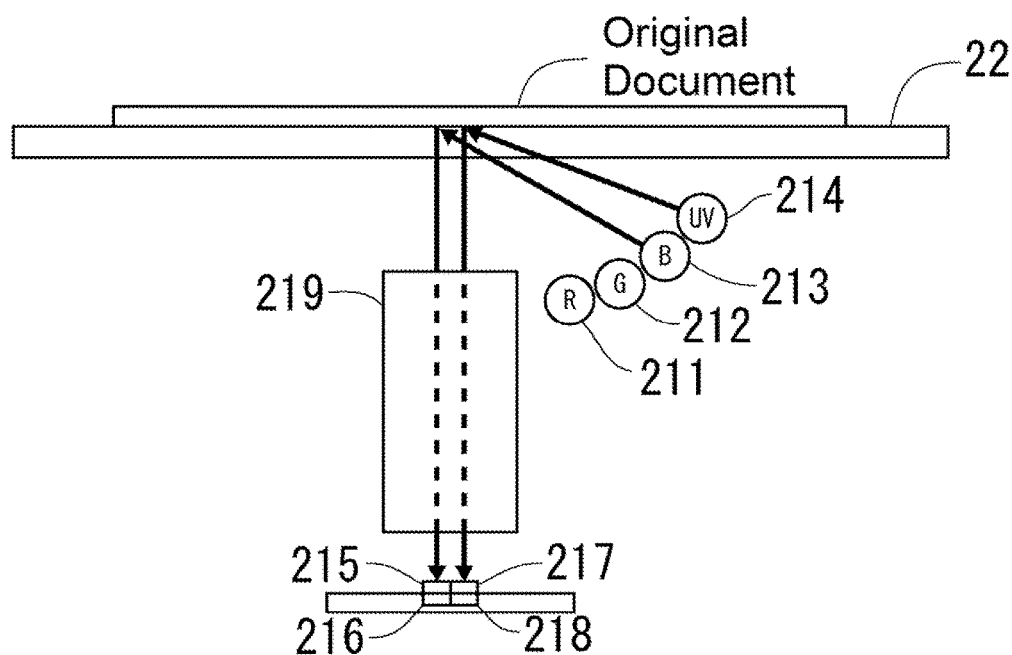

When reading one line in the original document, as illustrated in FIGS. 3A and 3B, the lighting control unit 241 switches between simultaneous lighting of the R light source 211 and the G light source 212 and simultaneous lighting of the B light source 213 and the UV light source 214.

Figure 4:
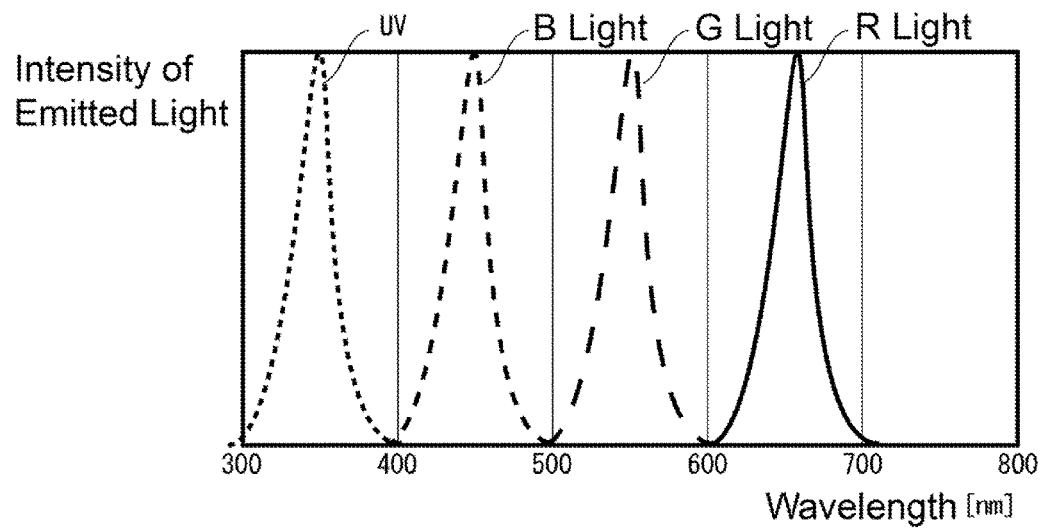
FIG. 4 illustrates spectral spectrum examples of an R light source, a G light source, a B light source, and a UV light source according to the one embodiment.
Figure 5:
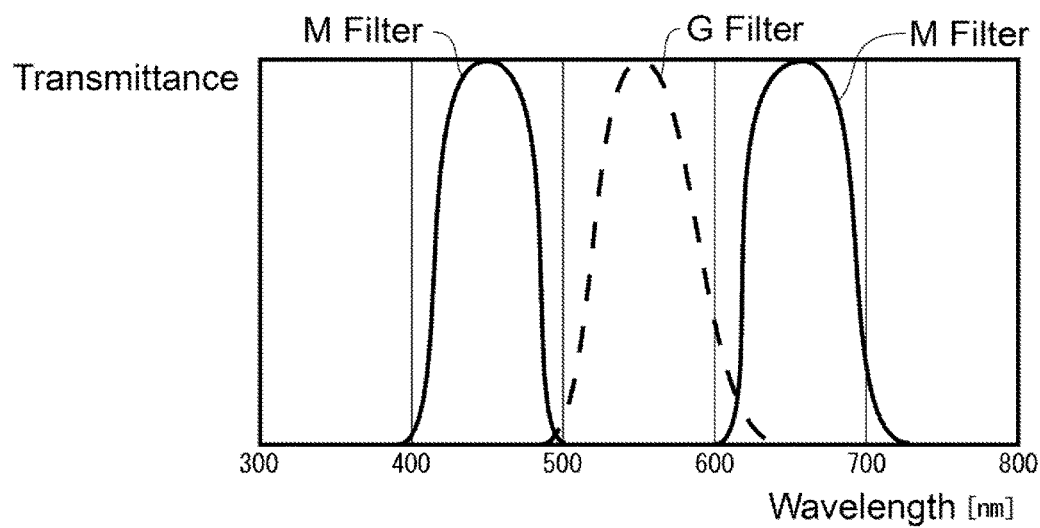
FIG. 5 illustrates spectral characteristic examples of an M filter and a G filter according to the one embodiment.

With reference to FIGS. 4 and 5, the M filter 215 transmits the R light irradiated from the R light source 211 and cuts off the G light irradiated from the G light source 212. Thus, when the R light source 211 and the G light source 212 simultaneously light, only the R light among the reflected lights from the original document enters the first photoelectric conversion element 216, and then the analog image signal output from the first photoelectric conversion element 216 becomes an R output indicating a luminance level of R component.

The G filter 217 cuts off the R light irradiated from the R light source 211 and transmits the G light irradiated from the G light source 212. Thus, when the R light source 211 and the G light source 212 simultaneously light, only the G light among the reflected lights from the original document enters the second photoelectric conversion element 218, and then the analog image signal output from the second photoelectric conversion element 218 becomes a G output indicating a luminance level of G component.

Furthermore, the M filter 215 transmits the B light irradiated from the B light source 213 and cuts off the UV light irradiated from the UV light source 214. Thus, when the B light source 213 and the UV light source 214 simultaneously light, only the B light among the reflected lights from the original document enters the first photoelectric conversion element 216, and then the analog image signal output from the first photoelectric conversion element 216 becomes a B output indicating a luminance level of B component.

Furthermore, the G filter 217 cuts off both the B light irradiated from the B light source 213 and the UV irradiated from the UV light source 214. Thus, when the B light source 213 and the UV light source 214 simultaneously light, and if a fluorescent color is not used in the original document, the reflected lights from the original document do not enter the second photoelectric conversion element 218.

In contrast to this, if a fluorescent color is used in the original document and when the UV light source 214 lights, as illustrated in FIG. 6, an ultraviolet light excites the fluorescent color to radiate a spectral energy in a visible light region, which the G filter 217 transmits. Thus, when the B light source 213 and the UV light source 214 simultaneously light and if a fluorescent color is used in the original document, only a radiated light from the fluorescent color enters the second photoelectric conversion element 218, and then the analog image signal output from the second photoelectric conversion element 218 becomes a UV output indicating presence/absence of a fluorescent color.

The A/D converter 242 converts the R output and the B output, which are output from the first photoelectric conversion element 216, and the G output and the UV output, which are output from the second photoelectric conversion element 218, into digital data.

The output unit 243 outputs the R output, the G output, and the B output, which are converted into the digital data, as the image data expressed by luminance signals of R, G, and B to the image forming unit 4 and outputs the UV output, which is converted into the digital data, as fluorescent color data indicating a fluorescent color region, to the image forming unit 4.

Then, the image forming unit 4 performs a color space conversion into a CYMK system on the received image data to form the respective colors toner images, so as to form the color image on the recording sheet. When the image forming unit 4 recognizes the fluorescent color region using the received fluorescent color data, the image forming unit 4 executes image processing for fluorescent color on the pixels inside the fluorescent color region in the received image data to approximate to the fluorescent color of the original document. The image forming unit 4, which functions as an image processing unit, executes, for example, image processing that increases saturation of the pixels inside the fluorescent color region and image processing where the pixels inside the fluorescent color region are replaced with approximated colors as the processing for fluorescent color.

While the radiated light from the fluorescent color enter also the first photoelectric conversion element 216 and is superimposed to the G output when the B light source 213 and the UV light source 214 simultaneously light, the radiated light from this fluorescent color is canceled out by referring to the UV output, the R output, and the B output to be converted into appropriate G data.

Typical document reading methods include: an RGB sequentially lighting method where photoelectric conversion elements aligned in one row sequentially switch respective R, G, and B light sources to read one line in an original document; and a color filter method where photoelectric conversion elements that include respective R, G, and B color filters and are aligned in three rows reads one line in an original document. While the RGB sequentially lighting method is inexpensive, its scanning speed is slow. While the color filter method is expensive, its scanning speed is fast.

In the RGB sequentially lighting method, when the UV light source is included, one line is read with four times of lighting, which leads to a further slow scanning speed. As in a typical technology, with the color filter method using the UV light source, one line is read with two times of lighting regardless of being expensive.

In contrast, according to the embodiment as described above, the document reading unit 2 that reads an original document as image data expressed by luminance signals of RGB includes: the R light source 211 that irradiates an original document with a red light; the G light source 212 that irradiates the original document with a green light; the B light source 213 that irradiates the original document with a blue light; the UV light source 214 that irradiates the original document with an ultraviolet light; the lighting control unit 241 that switches between simultaneous lighting of the R light source 211 and the G light source 212 and simultaneous lighting of the B light source 213 and the UV light source 214 when reading one line in the original document; the first photoelectric conversion element 216 that includes the M filter 215 that transmits the red light and the blue light and cuts off the green light and the ultraviolet light; the second photoelectric conversion element 218 that includes the G filter 217 that transmits the green light and cuts off the red light, the blue light, and the ultraviolet light; the lens 219 that guides reflected lights from the original document to the first photoelectric conversion element 216 and the second photoelectric conversion element 218; and the output unit 243 that outputs outputs of the first photoelectric conversion element 216 and the second photoelectric conversion element 218 at the time of simultaneous lighting of the R light source 211 and the G light source 212 and an output of the first photoelectric conversion element 216 at the time of simultaneous lighting of the B light source 213 and the UV light source 214 as the image data, and outputs an output of the second photoelectric conversion element 218 at the time of simultaneous lighting of the B light source 213 and the UV light source 214 as fluorescent color data indicating a fluorescent color region.

This configuration ensures two times of lighting of the first photoelectric conversion element 216 and the second photoelectric conversion element 218 aligned in two rows to read one line even when the UV light source 214 for detecting a fluorescent color is included in addition to the R light source 211, the G light source 212, and the B light source 213. This ensures distinguishing and reading a fluorescent color with a lower-price configuration than the color filter method without degrading its scanning speed compared with the RGB sequentially lighting method.

Furthermore, in the embodiment, the first photoelectric conversion element 216 outputs the R output indicating the luminance level of R component when the R light source 211 and the G light source 212 simultaneously light, and outputs the B output indicating the luminance level of B component when the B light source 213 and the UV light source 214 simultaneously light. The second photoelectric conversion element 218 outputs the G output indicating the luminance level of G component when the R light source 211 and the G light source 212 simultaneously light, and outputs the UV output indicating the presence/absence of a fluorescent color when the B light source 213 and the UV light source 214 simultaneously light.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A document reading unit that reads an original document as image data expressed by luminance signals of RGB, comprising:
 a contact image sensor, the contact image sensor including:
  an R light source that irradiates the original document with a red light;
  a G light source that irradiates the original document with a green light;
  a B light source that irradiates the original document with a blue light;
  a UV light source that irradiates the original document with an ultraviolet light;

a first photoelectric conversion element that includes an M filter, the M filter transmitting the red light and the blue light and cutting off the green light and the ultraviolet light;

a second photoelectric conversion element that includes a G filter, the G filter transmitting the green light and cutting off the red light, the blue light, and the ultraviolet light; and a lens that guides reflected lights from the original document to the first photoelectric conversion element and the second photoelectric conversion element;

a lighting control unit that switches between simultaneous lighting of the R light source and the G light source and simultaneous lighting of the B light source and the UV light source when reading one line in the original document; and an output unit, wherein the output unit outputs, as the image data, (i) an output of the first photoelectric conversion element and an output of the second photoelectric conversion element at the time of simultaneous lighting of the R light source and the G light source and (ii) an output of the first photoelectric conversion element at the time of simultaneous lighting of the B light source and the UV light source; and the output unit outputs an output of the second photoelectric conversion element at the time of simultaneous lighting of the B light source and the UV light source as fluorescent color data indicating a fluorescent color region.

2. The document reading unit according to claim 1, wherein:

the first photoelectric conversion element outputs an R output indicating a luminance level of R component when the R light source and the G light source simultaneously light, the first photoelectric conversion element outputting a B output indicating a luminance level of B component when the B light source and the UV light source simultaneously light; and the second photoelectric conversion element outputs a G output indicating a luminance level of G component when the R light source and the G light source simultaneously light, the second photoelectric conversion element outputting a UV output indicating presence/absence of a fluorescent color when the B light source and the UV light source simultaneously light.

3. An image processing apparatus comprising:

the document reading unit according to claim 1; and an image processing unit that executes image processing that increases saturation of pixels inside a fluorescent color region in the image data or image processing where the pixels inside the fluorescent color region are replaced with approximated colors when recognizing the fluorescent color region based on the fluorescent color data.

* * * * *